US008459360B2

(12) United States Patent
Pope et al.

(10) Patent No.: US 8,459,360 B2
(45) Date of Patent: Jun. 11, 2013

(54) DI-FUNCTIONAL SURFACTANTS FOR ENHANCED OIL RECOVERY

(75) Inventors: Gary A. Pope, Cedar Park, TX (US); Upali P. Weerasooriya, Austin, TX (US); Quoc P. Nguyen, Austin, TX (US); Larry N. Britton, Spicewood, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 308 days.

(21) Appl. No.: 12/874,920

(22) Filed: Sep. 2, 2010

(65) Prior Publication Data

US 2011/0048721 A1 Mar. 3, 2011

Related U.S. Application Data (60) Provisional application No. 61/239,310, filed on Sep. 2, 2009.

(51) Int. Cl.
*E21B 43/22* (2006.01)
*E21B 43/26* (2006.01)
*C09K 8/68* (2006.01)
*C09K 8/86* (2006.01)

(52) U.S. Cl.
USPC .......... 166/308.2; 166/270.1; 166/305.1; 507/252; 507/259; 507/260

(58) Field of Classification Search
None
See application file for complete search history.

(56) References Cited

U.S. PATENT DOCUMENTS

| 3,638,728 | A | * | 2/1972 | Hill | 166/270.1 |
|---|---|---|---|---|---|
| 3,811,504 | A | * | 5/1974 | Flournoy et al. | 166/270.1 |
| 3,858,656 | A | * | 1/1975 | Flournoy et al. | 166/270.1 |
| 4,043,396 | A | | 8/1977 | Kudchadker et al. | |
| 4,066,124 | A | * | 1/1978 | Carlin et al. | 166/252.3 |
| 4,463,806 | A | | 8/1984 | Hurd | |
| 4,703,797 | A | | 11/1987 | Djabbarah | |
| 4,828,032 | A | | 5/1989 | Teletzke et al. | |
| 5,074,358 | A | | 12/1991 | Rendall et al. | |
| 6,133,474 | A | * | 10/2000 | Rasheed et al. | 562/110 |
| 6,736,211 | B2 | * | 5/2004 | Berger et al. | 166/270.1 |
| 2004/0011526 | A1 | * | 1/2004 | Berger et al. | 166/275 |
| 2004/0102330 | A1 | | 5/2004 | Zhou et al. | |
| 2007/0191633 | A1 | | 8/2007 | Berger et al. | |
| 2008/0196893 | A1 | | 8/2008 | Berger et al. | |

OTHER PUBLICATIONS

Adkins. S., et al., "A New Process for Manufactur-ing and Stabilizing High-Performance EOR Surfac-tants at Low Cost for High-Tempera-ture. High Salin-ity Oil Reservoirs," Paper SPE 129923, presented at the 2010 SPE Improved Oil Recovery Symposium. Tulsa, Oklahoma, Apr. 24-28, 2010.

(Continued)

*Primary Examiner* — George Suchfield
(74) *Attorney, Agent, or Firm* — Kelly Kordzik; Matheson Keys & Kordzik PLLC (57) ABSTRACT

The present invention describes the synthesis and use of cleavable di-functional anionic surfactants for enhanced oil recovery applications and/or the use of sacrificial surfactants.

20 Claims, 4 Drawing Sheets

OTHER PUBLICATIONS

Dwarkanath. V., et al., "Using Co-Solvents to Provide Gradients and Improve Oil Recovery During Chemical Flooding in a Light Oil Reservoir," Paper SPE 113965, presented at the 2008 SPE Improved Oil Recovery Symposium, Tulsa, Oklahoma. Apr. 20-23, 2008.

Flaaten, A., "Experimental Study of Mioroemul-sion Characterization and Optimization in Enhamed Oil Recovery: A Design Approach for Reservoirs with High Salinity and Hardness," Thesis, The University of Texas at Austin (Dec. 2007).

Healy, R.N., et al. "Multiphase Microemuision Systems," Society of Petroleum Engineers Journal, 16(3), Jun. 1976; pp. 147-160; Society of Petroleum Engineers: US.

Huh, C., "Interfacial Tensions and Solubiizing Ability of a Microemulsion Phase That Coexists With Oil and Brine," Journal of Colloid and Interface Science. 71(2), Sep. 1979; pp. 408-426; Academic Press, Inc.; US.

Jackson, A.C., 2006, "Experimental Study of the Benefits of Sodium Carbonate on Surfactants for EOR," Thesis, The University of Texas at Austin (Dec. 2006).

Winsor, Von P.A., "Solvent Properties of Amphiphilic Compounds," Butterworths Scientific Publ, Ltd. (London 1954).

Yang, H., et al., "Low-Cost, High Performance Chemicals for Enhanced Recovery," Paper SPE 129978, presented at the 2010 SPE Improved Oil Recovery Symposium, Tulsa, Oklahoma, Apr. 24-28, 2010.

Zhao, Ping, "Development of High-Performance Surfactants for Difficult Oils," Thesis, The University of Texas at Austin (Dec. 2007).

Korea International Searching Authority; International Search Report & Written Opinion for PCT/US2010/047717; May 24, 2011; Korean Patent Office, KR.

* cited by examiner

Scheme 2

FIG. 5

DI-FUNCTIONAL SURFACTANTS FOR ENHANCED OIL RECOVERY

CROSS-REFERENCE TO RELATED PATENT APPLICATION

This Application for Patent claims the benefit of priority from U.S. Provisional Patent Application Ser. No. 61/239,310, filed Sep. 2, 2009, entitled "Di-Functional Surfactants For Enhanced Oil Recovery," which provisional patent application is commonly assigned to the assignee of the present invention, and which disclosure is considered part of and is incorporated by reference in its entirety in the disclosure of this application.

TECHNICAL FIELD OF THE INVENTION

The present invention relates in general to the field of oil recovery, and more particularly, to the design and synthesis of a novel di-functional anionic surfactant compounds for enhanced oil recovery (EOR) applications.

BACKGROUND OF THE INVENTION

Without limiting the scope of the invention, its background is described in connection with the compositions and compounds for oil recovery applications.

U.S. Pat. No. 5,074,358 issued to Rendall et al. (1991) discloses a foam for use in a subterranean oil-bearing formation for reducing and controlling the mobility of a gaseous drive fluid. According to the '348 patent the foam is generated using an inert gas and a fluorocarbon surfactant solution in admixture with an amphoteric or anionic hydrocarbon surfactant solution.

United States Patent Application No. 20080196893 (Berger and Berger, 2008) describes a process for the recovery of oil from subterranean reservoirs by injecting an aqueous fluid containing from about 0.05 to about 2.0% by weight of a bi-functional surfactant or a mixture of surfactants containing one or more of the following structures:

Optionally the aqueous fluid may contain mixtures of individual surfactants having carboxylic, and sulfonate or sulfate functionalities. The remainder of the composition includes water or brine, a cosolvent and optionally a viscosity control agent, and optionally an alkali.

SUMMARY OF THE INVENTION

The present invention describes the synthesis of novel surfactant molecules used in EOR. The surfactants described in the present invention are high molecular weight sulfated internal olefin sulfonate (IOS) sulfates and high molecular weight dialkylphenol alkoxylate sulfonate sulfates.

In general, in one aspect, the invention features a method that includes a method of treating a hydrocarbon-bearing formation which method includes selecting a composition that includes a cleavable di-functional anionic surfactant. The di-functional anionic surfactant is sufficiently soluble in water such that the di-functional anionic surfactant can be injected into the hydrocarbon-bearing formation. The method further includes injecting the composition into the hydrocarbon-bearing formation. Once in the hydrocarbon-bearing formation, the di-functional anionic surfactant cleaves and releases a highly surface active mono-functional sulfonate in the formation.

Implementations of the invention can include one or more of the following features:

The composition can further include a sacrificial surfactant.

The sacrificial surfactant can further be hydrolyzable and may form an alcohol under downhole conditions.

The hydrocarbon-bearing formation can be downhole.

The downhole conditions can include a pressure in a range from about 1 bar to 1000 bars and a temperature in a range of from about 70° F. to 400° F.

The method can further include fracturing the hydrocarbon formation. The composition can be injected into the hydrocarbon-bearing formation during the fracturing, after the fracturing, or both during and after fracturing.

The hydrocarbon-bearing formation can have a wellbore therein. The method can further include obtaining hydrocarbons from the wellbore after injecting the composition into the hydrocarbon-bearing formation.

The di-functional anionic surfactant can be of the formula (I):

$R_1$ and $R_2$ can be the same or different. $R_1$ and $R_2$ can each be an alkyl group or hydrogen. $R_1$ and $R_2$ combined can include 10 to 40 carbon atoms.

$R_1$ and $R_2$ can each be an alkyl group

The di-functional anionic surfactant can be of the formula (II):

$R_1$ and $R_2$ can be the same or different. $R_1$ and $R_2$ can each be an alkyl group or hydrogen. $R_1$ and $R_2$ combined can include 10 to 40 carbon atoms.

$R_1$ and $R_2$ can each be an alkyl group

The di-functional anionic surfactant can be a di-functional anionic surfactant of the formula (I), a di-functional anionic surfactant of formula (II), or a combination thereof:

(I)

(II)

The sacrificial surfactant can be a surfactant from the group of dialkyl sulfosuccinates and their alkoxylated homologues, monoalkyl sulfosuccinates and their alkoxylated versions, mono alkyl succinates and their alkoxylated versions, and alcohol alkoxysulfates. The dialkyl sulfosuccinates, monoalkyl sulfosuccinates, and mono alkyl succinates of this group can include linear or branched $C_4$-$C_{16}$ saturated or unsaturated chains, polyethoxy or polypropoxy chains with a degree of polymerization ranging from 0-12, $C_4$-$C_{12}$ alkylphenol structures, or combinations thereof. The alcohol alkoxysulfates of this group can include linear or branched $C_6$-$C_{32}$ chains, polyethoxy or polypropoxy chains with a degree of polymerization ranging from 0-50, $C_4$-$C_{12}$ alkylphenol structures or combinations thereof.

The composition can be cleavable at reservoir pH, temperature, pressure, or a combination thereof.

The composition can be cleavable by the introduction of a catalyst into the formation.

The composition can include a high molecular weight sulfated internal olefin sulfonate.

The composition can include a high molecular weight Dialkylphenol alkoxylate sulfonate sulfate.

In general, in another aspect, the invention features a method of treating a hydrocarbon-bearing formation that includes selecting a composition that includes a cleavable di-functional anionic surfactant and a sacrificial surfactant. The combination of the di-functional anionic surfactant and the sacrificial surfactant is sufficiently soluble in water such that combination can be injected into the hydrocarbon-bearing formation. The method further includes injecting the composition into the hydrocarbon-bearing formation. The di-functional anionic surfactant cleaves and releases a highly surface active mono-functional sulfonate in the formation.

Implementations of the invention can include one or more of the following features:

The sacrificial surfactant can be hydrolyzable and form an alcohol under downhole conditions.

In general, in another aspect, the invention features a method of treating a hydrocarbon-bearing formation that includes injecting a composition into the hydrocarbon-bearing formation. The composition includes a first surfactant and a sacrificial surfactant. The sacrificial surfactant causes the first surfactant to become sufficiently soluble in water to be injected into the hydrocarbon-bearing formation.

Implementations of the invention can include one or more of the following features:

The sacrificial surfactant can be hydrolyzable and may form an alcohol under downhole conditions.

The sacrificial surfactants can be a surfactant from the group of dialkyl sulfosuccinates and their alkoxylated homologues, mono alkyl sulfosuccinates and their alkoxylated versions, mono alkyl succinates, mono alkyl maleates and their alkoxylated versions, and alcohol alkoxysulfates.

In general, in another aspect, the invention features a method of synthesizing a di-functional anionic surfactant of formula (I).

The method includes the steps of deriving an acid treated intermediate cyclic sultone using a process that includes sulfonating a solution of an internal olefin. The internal olefin has a general formula $R_1$—$C_4H_6$—$R_2$. $R_1$ and $R_2$ can be the same or different. $R_1$ and $R_2$ can each be an alkyl group or hydrogen. $R_1$ and $R_2$ combined can include 10 to 40 carbon atoms. The method further includes neutralizing and hydrolyzing the acid treated intermediate cyclic sultone to yield the di-functional anionic surfactant of formula (I). The method further includes recovering the di-functional anionic surfactant of formula (I) from the reaction mixture.

$R_1$ and $R_2$ can each be an alkyl group.

Implementations of the invention can include one or more of the following features:

The step of deriving the acid treated intermediate cyclic sultone can include sulfonating the solution of the internal olefin with sulfur trioxide in air to derive an intermediate cyclic sultone. The step of deriving the acid treated intermediate cyclic sultone can further include treating the intermediate cyclic sultone with an acid. The acid used for treating the intermediate cyclic sultone can be sulfuric acid.

The step of deriving the acid treated intermediate cyclic sultone can include sulfonating the solution of the internal olefin with a sulfating mixture of sulfuric acid and sulfur trioxide to derive the acid treated intermediate cyclic sultone.

In general, in another aspect, the invention features a method of synthesizing a di-functional anionic of formula (II).

(II)

The method includes alkoylating a dinonylphenol to yield an intermediate alkoxylate derivative. The step of alkoxylating is performed using ethylene oxide, propylene oxide, or a mixture of both. The method further includes treating the intermediate alkoyxlate derivative with a sulfur trioxide in air to form an intermediate sulfonated alkoxylate derivative. The method further includes neutralizing and hydrolyzing the intermediate sulfonated alkoxylate derivative with a base to yield the di-functional anionic surfactant of formula (II). The method further includes recovering the di-functional anionic surfactant of formula (II) from the reaction mixture. $R_1$ and $R_2$ can be the same or different. $R_1$ and $R_2$ can each be an alkyl group or hydrogen. $R_1$ and $R_2$ combined can include 10 to 40 carbon atoms.

$R_1$ and $R_2$ can each be an alkyl group.

In general, in another aspect, the invention features a composition for treating a hydrocarbon-bearing formation. The composition includes a cleavable di-functional anionic surfactant. The di-functional anionic surfactant is sufficiently soluble in water such that the di-functional anionic surfactant can be injected into a hydrocarbon-bearing formation. The di-functional anionic surfactant is operable under downhole conditions such that, upon injection into the hydrocarbon-bearing formation, the di-functional anionic surfactant is cleavable and operably able to release a highly surface active monofunctional sulfonate.

Implementations of the invention can include one or more of the following features:

The composition can further include a sacrificial surfactant.

The di-functional anionic surfactant can be of the formula (I):

$R_1$ and $R_2$ can be the same or different. $R_1$ and $R_2$ can each be an alkyl group or hydrogen. $R_1$ and $R_2$ combined can include 10 to 40 carbon atoms.

$R_1$ and $R_2$ can each be an alkyl group.

The di-functional anionic surfactant can be of the formula (II):

$R_1$ and $R_2$ can be the same or different. $R_1$ and $R_2$ can each be an alkyl group or hydrogen. $R_1$ and $R_2$ combined can include 10 to 40 carbon atoms.

$R_1$ and $R_2$ can each be an alkyl group.

The composition can include a sacrificial surfactant. The cleavable di-functional anionic surfactant can be a di-functional anionic surfactant of formula (I), a di-functional anionic surfactant of formula (II), or a combination thereof. Formula (I) and Formula (II) are, respectively:

The sacrificial surfactant can be hydrolyzable and can form an alcohol under downhole conditions.

The sacrificial surfactant can be from the group of dialkyl sulfosuccinates and their alkoxylated homologues, monoalkyl sulfosuccinates and their alkoxylated versions, mono alkyl succinates and their alkoxylated versions, alcohol alkoxysulfates, and combinations thereof The dialkyl sulfosuccinates, monoalkyl sulfosuccinates, and mono alkyl succinates can further include linear or branched $C_4$-$C_{16}$ saturated or unsaturated chains, polyethoxy or polypropoxy chains with a degree of polymerization ranging from 0-12, $C_4$-$C_{12}$ alkylphenol structures or combinations thereof. The alcohol alkoxysulfates can further include linear or branched $C_6$-$C_{32}$ chains, polyethoxy or polypropoxy chains with a degree of polymerization ranging from 0-50, $C_4$-$C_{12}$ alkylphenol structures or combinations thereof.

The composition can be cleavable at reservoir pH, temperature, pressure, or a combination thereof.

The composition can be cleavable in the presence of a catalyst in the formation.

The composition can include a high molecular weight sulfated internal olefin sulfonate.

The composition can include a high molecular weight Dialkylphenol alkoxylate sulfonate sulfate.

In general, in another aspect, the invention features a composition for treating a hydrocarbon-bearing formation. The composition includes a cleavable di-functional anionic surfactant and a sacrificial surfactant. The combination of the di-functional anionic surfactant and the sacrificial surfactant is sufficiently soluble in water such that the combination can injected into a hydrocarbon-bearing formation. The di-functional anionic surfactant is operable under downhole conditions such that, upon injection into the hydrocarbon-bearing formation, the di-functional anionic surfactant is cleavable and operably able to release a highly surface active monofunctional sulfonate.

Implementations of the invention can include one or more of the following features:

The sacrificial surfactant can be hydrolyzable and can form an alcohol under downhole conditions.

In general, in another aspect, the invention features a composition for treating a hydrocarbon-bearing formation. The composition includes a first surfactant and a sacrificial surfactant. The sacrificial surfactant in the composition operatively causes the first surfactant to become sufficiently soluble in water to be injected into a hydrocarbon-bearing formation.

Implementations of the invention can include one or more of the following features:

The sacrificial surfactant can be hydrolyzable and can form an alcohol under downhole conditions.

The sacrificial surfactant can be selected from the group of dialkyl sulfosuccinates and their alkoxylated homologues, mono alkyl sulfosuccinates and their alkoxylated versions, monoalkyl succinates, monoalkyl maleates and their alkoxylated versions, and alcohol alkoxysulfates.

In general, in another aspect, the invention features a di-functional anionic surfactant of formula (I):

$R_1$ and $R_2$ can be the same or different. $R_1$ and $R_2$ can each be an alkyl group or hydrogen. $R_1$ and $R_2$ combined can include 10 to 40 carbon atoms.

$R_1$ and $R_2$ can each be an alkyl group. $R_1$ and $R_2$ can each include 8 to 20 carbon atoms.

In general, in another aspect, the invention features a di-functional anionic surfactant of formula (II):

(II)

$R_1$ and $R_2$ can be the same or different. $R_1$ and $R_2$ can each be an alkyl group or hydrogen. $R_1$ and $R_2$ combined can include 10 to 40 carbon atoms.

$R_1$ and $R_2$ can each be an alkyl group. $R_1$ and $R_2$ can each include 8 to 20 carbon atoms.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention describes the synthesis and use of a high molecular weight di-functional anionic surfactant composed of one hydrolytically stable functional group and another group capable of being labile under controlled conditions. The stable group could be a sulfonate functionality where as the to-be labile one could be a sulfate moiety. Thus, a surfactant molecule, as such, can be an alkyl sulfonate-sulfate. The present invention demonstrates the intermolecular sacrificial surfactant concept. The present invention uses an alcohol ether sulfate (ES) as the solubilizing sacrificial agent with the primary surfactant which was a sulfonate.

The compositions and methods taught herein provide for novel strategies for treating a hydrocarbon-bearing formation, in which a di-functional surfactant is injected into a hydrocarbon-bearing formation in need of enhanced oil recovery, wherein the cleavable di-functional anionic surfactant is sufficiently soluble in water to be injected into a hydrocarbon-bearing formation and upon injection into the formation is cleavable and releases a highly surface active monofunctional sulfonated under downhole conditions.

Many surfactants used for enhanced oil recovery are not sufficiently soluble in brine unless large quantities of co-surfactants and/or co-solvents are used. With some oils, especially those with a higher molecular weight or higher wax content and under some reservoir conditions such as high temperature, commonly used surfactants become less soluble in the oil, so the hydrophobe size of the surfactant must increase correspondingly to provide the desired surface activity and generate lower interfacial tension. Consequently, the solubility problem of the surfactant becomes worse until there is no practical solution even using expensive solubilizer co-surfactants and/or co-solvents. The present invention addresses this issue by the incorporation of an extra hydrophilic functional group in the anionic surfactant molecule which then assumes a di-functional structure. This, in turn, makes the surfactant sufficiently soluble in water so that it can be injected into oil reservoirs to increase oil production. However, when it is time to interact with the reservoir oil, this extra functional group needs to be cleaved-off from the di-functional surfactant molecule thereby generating a highly surface active mono-functional sulfonate. For example, this extra functional group can be a sulfate moiety which needs to be cleavable as a function of reservoir temperature and pH and the stable functional group of the surfactant molecule can be a sulfonate functionality. The cleavage of this extra hydrophilic group is very important and central to this invention and being able to do so when desired thus becomes extremely important.

Figure 2:
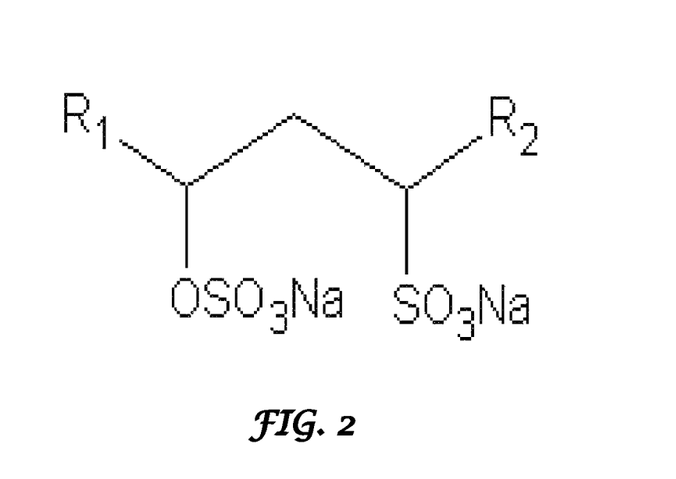
FIG. 2 shows the structure of alkane sulfonate-sulfate according to one embodiment of the present invention.
Figure 3:
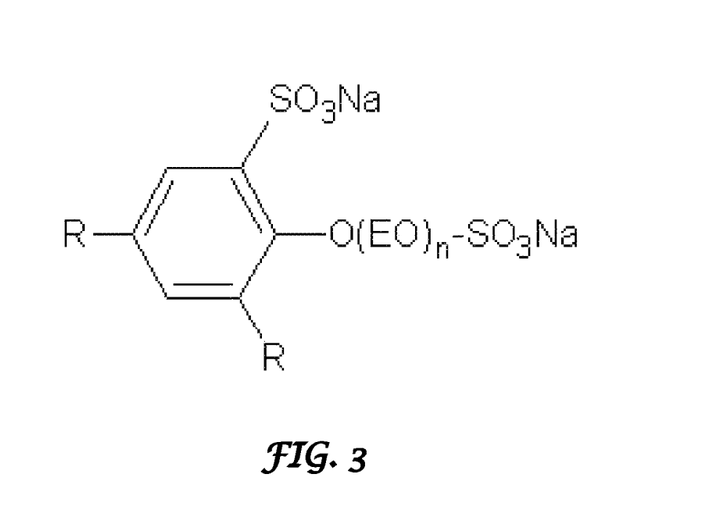
FIG. 3 shows the structure of the dialkylphenol alkoxylate sulfonate sulfate according to one embodiment of the present invention.

The present invention describes two novel key molecules to demonstrate this concept in Enhanced Oil Recovery (EOR). The surfactants are A) high molecular weight sulfated internal olefin sulfonate (IOS) sulfate and B) high molecular weight dialkylphenol alkoxylate sulfonate sulfate. Both these molecules contain double hydrophilic anions with the labile group being the sulfate moiety. It is this sulfate group that could be "programmed" to be cleaved off later on, according to the above mentioned invention. The structure of IOS sulfate and the process of making it is novel. Even though Monoalkyl phenol alkoxylates sulfonate sulfates have appeared in the literature, the Dialkyl version is unknown at present. The representative structures of the IOS and the dialkylphenol alkoxylate sulfonate are represented in FIGS. 2 and 3 respectively.

The di-functional surfactant molecules of the present invention are synthesized as described below.

Figure 4:
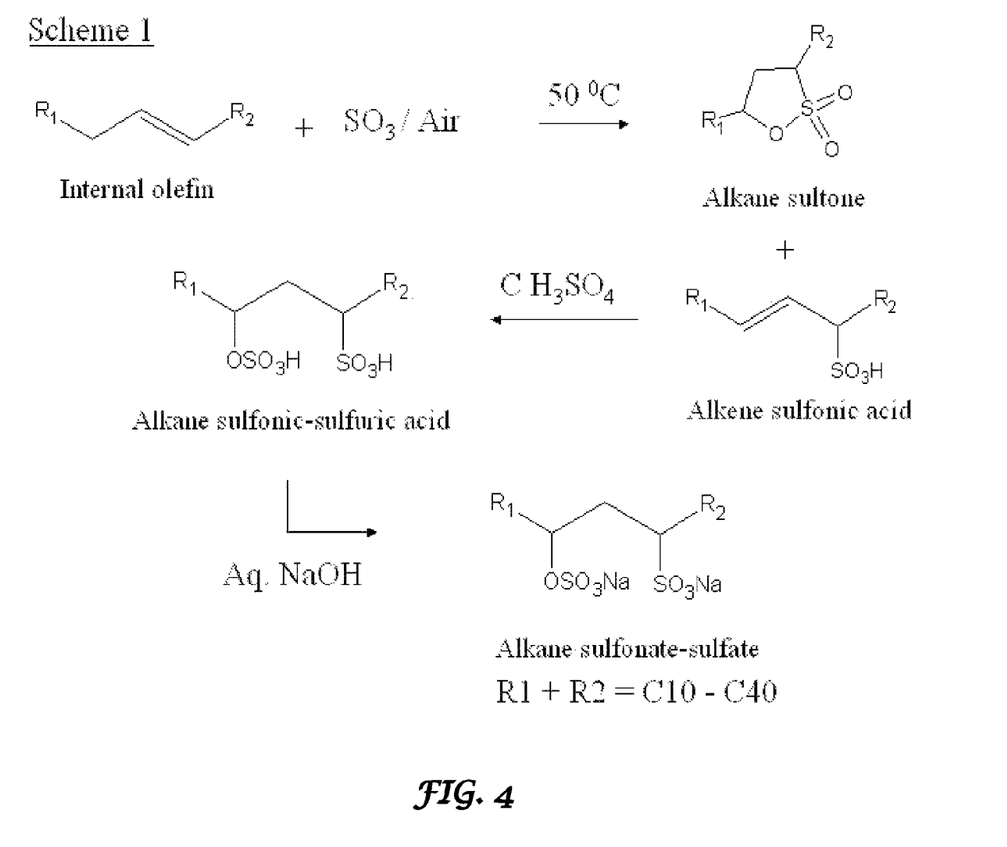
FIG. 4 is a schematic representation of the synthesis method for the alkane sulfonate sulfate surfactant.

High molecular weight IOS sulfate: The IOS is manufactured by sulfonation of a high molecular weight internal olefin, followed by additional processing including neutralization. The intermediate formed during this sulfonation is a cyclic sultone. Treating this sultone with sulfuric acid followed by neutralization results in the IOS sulfate. Alternatively, a mixture of sulfuric acid and Sulfur Trioxide can be used as the sulfonating-sulfating agent followed by neutralization to produce IOS sulfate. FIG. 4 is a schematic representation of the synthesis method for the IOS surfactant.

Figure 5:
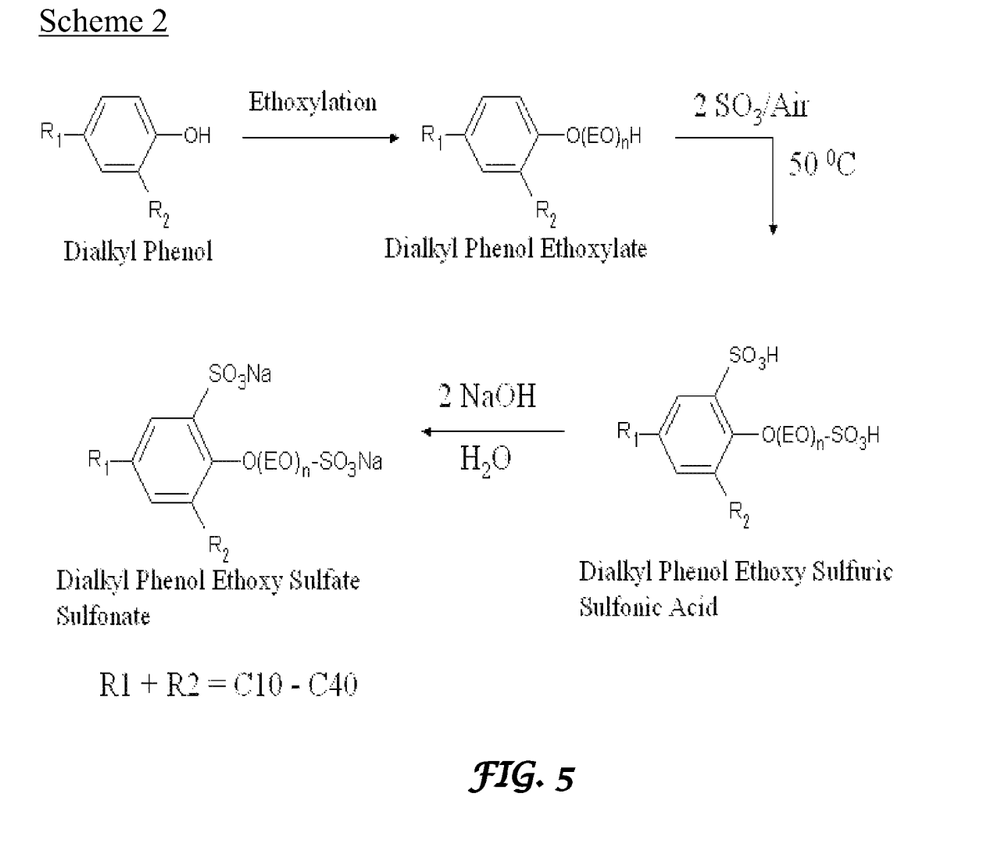
FIG. 5 is a schematic representation of the synthesis method for the Dialkylphenol alkoxylate sulfonate sulfate surfactant.

Dialkylphenol alkoxylate sulfonate sulfate: The Dialkylphenol is chosen as the hydrophobe as it is difficult to make a very long chain monoalkylphenol. Thus, a Dialkylphenol such as dinonylphenol is first alkoxylated with EO and/or PO to make the alkoxylate. This is then treated with sulfur trioxide first, followed by neutralization to produce the Dialkylphenol alkoxylate sulfonate sulfate. FIG. 5 is a schematic representation of the synthesis method for the Dialkylphenol alkoxylate sulfonate sulfate surfactant.

The following definitions of terms apply throughout the specification and claims.

For methods of treating a hydrocarbon-bearing formation and/or a well bore, the term "treating" includes placing a chemical (e.g., a fluorochemical, cationic polymer, or corrosion inhibitor) within a hydrocarbon-bearing formation using any suitable manner known in the art (e.g., pumping, injecting, pouring, releasing, displacing, spotting, or circulating the chemical into a well, well bore, or hydrocarbon-bearing formation.

The term "polymer" refers to a molecule having a structure that essentially includes the multiple repetition of units derived, actually or conceptually, from molecules of low relative molecular mass. The term "polymer" includes "oligomer".

The term "bonded" refers to having at least one of covalent bonding, hydrogen bonding, ionic bonding, Van der Waals interactions, pi interactions, London forces, or electrostatic interactions.

"Alkyl group" and the prefix "alk-" are inclusive of both straight chain and branched chain groups and of cyclic groups having up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms.

"Alkylene" is the divalent form of the "alkyl" groups defined above.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Arylene" is the divalent form of the "aryl" groups defined above.

Figure 1:
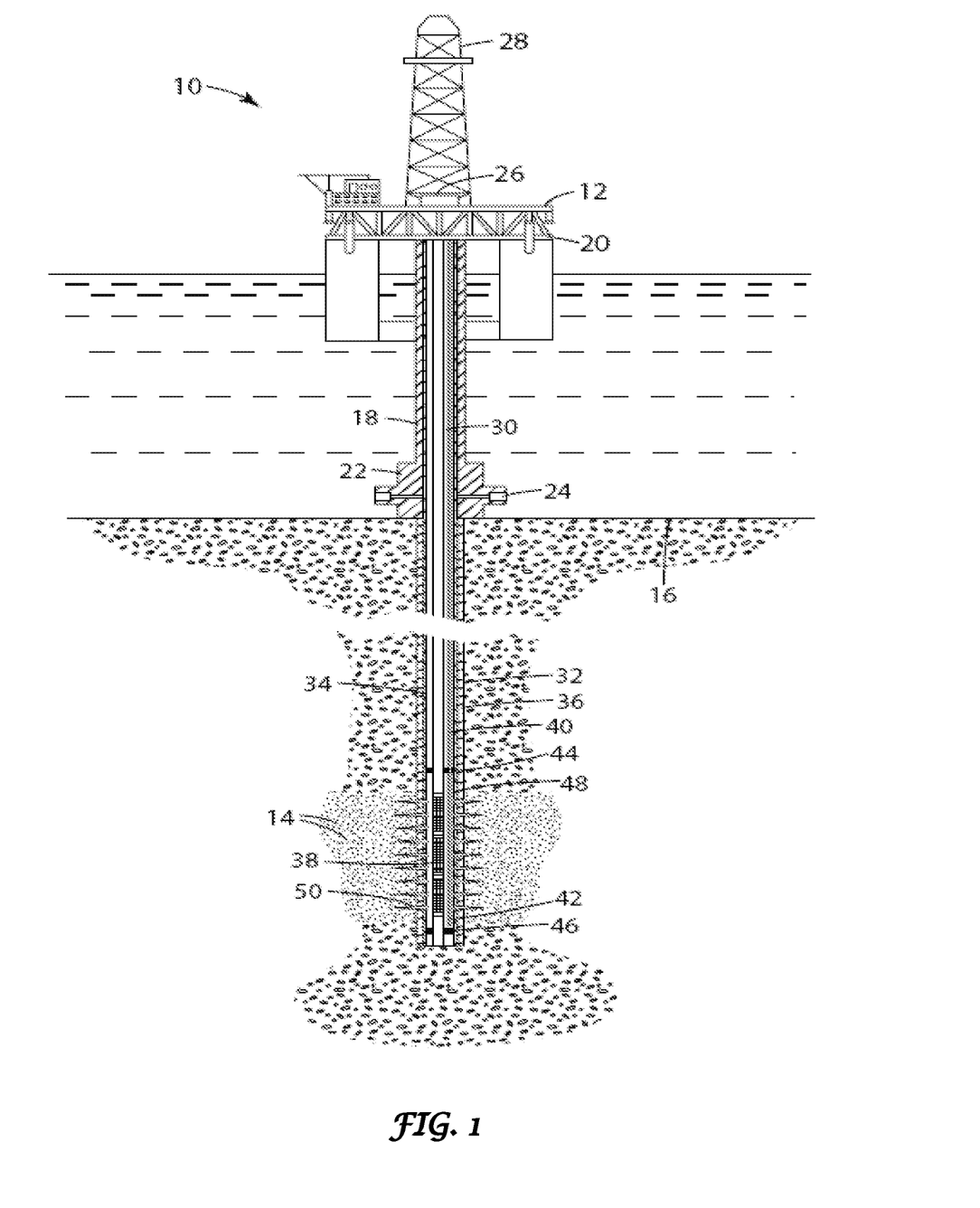
FIG. 1 is a schematic illustration of an offshore oil platform with facilities for injecting chemical solutions into the reservoir for the purpose of flooding the reservoir to enhance the oil recovery according to some embodiments of the present invention.

Referring to FIG. 1, an exemplary offshore oil platform is schematically illustrated and generally designated 10. Semi-submersible platform 12 is centered over submerged hydrocarbon-bearing formation 14 located below sea floor 16. Subsea conduit 18 extends from deck 20 of platform 12 to wellhead installation 22 including blowout preventers 24. Platform 12 is shown with hoisting apparatus 26 and derrick 28 for raising and lowering pipe strings such as work string 30.

Wellbore 32 extends through the various earth strata including hydrocarbon-bearing formation 14. Casing 34 is cemented within wellbore 32 by cement 36. Work string 30 may include various tools including, for example, sand control screen assembly 38 which is positioned within wellbore 32 adjacent to hydrocarbon-bearing formation 14. Also extending from platform 12 through wellbore 32 is fluid delivery tube 40 having fluid or gas discharge section 42 positioned adjacent to hydrocarbon-bearing formation 14; shown with production zone 48 between packers 44, 46. When it is desired to treat the near-wellbore region of hydrocarbon-bearing formation 14 adjacent to production zone 48, work string 30 and fluid delivery tube 40 are lowered through casing 34 until sand control screen assembly 38 and fluid discharge section 42 are positioned adjacent to the near-wellbore region of hydrocarbon-bearing formation 14 including perforations 50. Thereafter, a composition described herein is pumped down delivery tube 40 to progressively treat the near-wellbore region of hydrocarbon-bearing formation 14.

In the figures, FIG. 2 shows the structure of alkane sulfonate-sulfate according to one embodiment of the present invention. FIG. 3 shows the structure of the dialkylphenol alkoxylate sulfonate sulfate according to one embodiment of the present invention. FIG. 4 is a schematic representation of the synthesis method for the alkane sulfonate sulfate surfactant. FIG. 5 is a schematic representation of the synthesis method for the Dialkylphenol alkoxylate sulfonate sulfate surfactant.

Phase Behavior Procedures.

Phase Behavior Screening.

Phase behavior experiments are used to characterize chemicals for EOR. There are many benefits in using aqueous and microemulsion phase behavior tests as a screening method. Phase Behavior tests are used to determine and observe among other important characteristics: (1) the effect of electrolytes; (2) oil and water solubilization, (3) 1 FT reduction; (4) presence or absence of gels, liquid crystals, macroemulsions and other undesirable phases; (5) micro emulsion and macroemulsion viscosities; (6) macro emulsion coalescence times; (7) identify optimal surfactant-cosurfactant-cosolvent-alkali-polymer formulations; and/or (7) identify optimal formulations for coreflood and reservoir experiments.

A thermodynamically stable phase called a microemulsion can form with oil, water and surfactant mixtures. Surfactants form micellar structures in aqueous solutions at concentrations above the critical micelle concentration (CMC). When oil is added to the aqueous solution and mixed with it to form an emulsion, the emulsion sometimes coalesces into a separate phase at the oil-water interfaces and is referred to as a microemulsion. A microemulsion is a stable surfactant-rich distinct phase consisting of surfactant, oil and water and possibly co-solvents and other components. This phase is thermodynamically stable in the sense that it will return to the same phase volume and composition at a given temperature. Some workers in the past have added additional requirements, but for the purposes of this engineering study, the only requirement will be that the microemulsion is a thermodynamically stable phase.

The phase transition is examined by keeping all variables fixed except for the scanning variable. The scan variable is changed over a series of pipettes and may include, but is not limited to, salinity, temperature, chemical (surfactant, alcohol, electrolyte, alkali, polymer), oil, which is sometimes characterized by its equivalent alkane carbon number (EACN), and surfactant structure, which is sometimes characterized by its hydrophilic-lipophilic balance (HLB). The phase transition was first characterized by Winsor (1954) into three regions: Type I—excess oleic phase, Type III—aqueous, microemulsion and oleic phases, and the Type II—excess aqueous phase. The phase transition boundaries and some common terminology are described as follows: Type I to III—lower critical salinity, Type III to II—upper critical salinity, oil solubilization ratio (Vo/Vs), water solubilization ratio (Vw/Vs), the solubilization value where the oil and water solubilization ratios are equal is called the Optimum Solubilization Ratio ($\sigma^*$), and the electrolyte concentration where the optimum solubilization ratio occurs is referred to as the Optimal Salinity ($S^*$).

Determining Interfacial Tension. Efficient use of time and lab resources can lead to valuable results when conducting phase behavior scans. A correlation between oil and water solubilization ratios and interfacial tension was suggested by Healy and Reed (1976) and a theoretical relationship was later derived by Chun Huh (1979). Lowest oil-water 1 FT occurs at optimum solubilization ratio as shown by the Chun Huh theory. This is equated to an interfacial tension through the Chun Huh equation, where IFT varies with the inverse square of the solubilization ratio:

$$\gamma = \frac{C}{\sigma^2}$$

For most crude oils and microemulsions, C=0.3 is a good approximation. Therefore, a quick and convenient way to estimate 1 FT is to measure phase behavior and use the Chun-Huh equation to calculate 1 FT. The 1 FT between microemulsions and water and/or oil can be very difficult and time consuming to measure and is subject to larger errors, so using the phase behavior approach to screen hundreds of combinations of surfactants, co-surfactants, co-solvents, electrolytes, oil, and so forth is not only simpler and faster, but avoids the measurement problems and errors associated with measuring 1 FT especially of combinations that show complex behavior (gels and so forth) and will be screened out anyway. Once a good formulation has been identified, then it is still a good idea to measure IFT.

Equipment. Phase behavior experiments are created with the following materials and equipment.

Mass Balance. Mass balances are used to measure chemicals for mixtures and determine initial saturation values of cores.

Water Deionizer. Deionized (DI) water is prepared for use with all the experimental solutions using a Nanopure™ filter system. This filter uses a recirculation pump and monitors the water resistivity to indicate when the ions have been removed. Water is passed through a 0.45 micron filter to eliminate undesired particles and microorganisms prior to use.

Borosilicate Pipettes. Standard 5 mL borosilicate pipettes with 0.1 mL markings are used to create phase behavior scans as well as run dilution experiments with aqueous solutions. Ends are sealed using a propane and oxygen flame.

Pipette Repeater. An Eppendorf Repeater Plus® instrument is used for most of the pipetting. This is a handheld dispenser calibrated to deliver between 25 microliter and 1 ml increments. Disposable tips are used to avoid contamination between stocks and allow for ease of operation and consistency.

Propane-oxygen Torch. A mixture of propane and oxygen gas is directed through a Bernz-O-Matic flame nozzle to create a hot flame about ½ inch long. This torch is used to flame-seal the glass pipettes used in phase behavior experiments.

Convection Ovens. Several convection ovens are used to incubate the phase behaviors and core flood experiments at the reservoir temperatures. The phase behavior pipettes are primarily kept in Blue M and Memmert ovens that are monitored with mercury thermometer and oven temperature gauges to ensure temperature fluctuations are kept at a minimal between recordings. A large custom built flow oven was used to house most of the core flood experiments and enabled fluid injection and collection to be done at reservoir temperature.

pH Meter. An ORION research model 701/digital ionalyzer with a pH electrode is used to measure the pH of most aqueous samples to obtain more accurate readings. This is calibrated with 4.0, 7.0 and 10.0 pH solutions. For rough measurements of pH, indicator papers are used with several drops of the sampled fluid.

Phase Behavior Calculations. The oil and water solubilization ratios are calculated from interface measurements taken from phase behavior pipettes. These interfaces are recorded over time as the mixtures approached equilibrium and the volume of any macroemulsions that initially formed decreased or disappeared. The procedure for creating phase behavior experiments will be discussed later.

Oil Solubilization Ratio. The oil solubilization ratio is defined as the volume of oil divided by the volume of surfactant in the microemulsion. All the surfactant is presumed to be in the microemulsion phase. The oil solubilization ratio is applied for Winsor type I and type III behavior. The volume of oil solubilized is found by reading the change between initial aqueous level and excess oil (top) interface level. The oil solubilization ratio is calculated as follows:

$$\sigma_o = \frac{V_o}{V_s} \quad (4.1)$$

$\sigma_o$=oil solubilization ratio
$V_o$=volume of oil solubilized
$V_s$=volume of surfactant Water Solubilization Ratio. The water solubilization ratio is defined as the volume of water divided by the volume of surfactant in microemulsion. All the surfactant is presumed to be in the microemulsion phase. The water solubilization ratio is applied for Winsor type III and type II behavior. The volume of water solubilized is found by reading the change between initial aqueous level and excess water (bottom) interface level. The water solubilization ratio is calculated as follows:

$$\sigma_w = \frac{V_w}{V_s} \quad (4.2)$$

$\sigma_w$=water solubilization ratio
$V_w$=volume of water solubilized

Optimum Solubilization Ratio. The optimum solubilization ratio occurs where the oil and water solubilization ratios are equal. The nature of phase behavior screening often does not include a data point at optimum, so the solubilization ratio curves are drawn for the oil and water solubilization ratios and the intersection of these two curves is defined as the optimum. The following is true for the optimum solubilization ratio:

$\sigma_o=\sigma_w=\sigma^*$
$\sigma$=optimum solubilization ratio

Phase Behavior Methodology. The methods for creating, measuring and recording observations are described in this section. Scans are made using a variety of electrolyte mixtures described below. Oil is added to most aqueous surfactant solutions to see if a microemulsion formed, how long it took to form and equilibrate if it does form, what type of microemulsion formed and some of its properties such as viscosity. However, the behavior of aqueous mixtures without oil added is also important and is also done to determine if the aqueous solution is clear and stable over time as desired, or becomes cloudy or separated into more than one phase over time.

Preparation of samples. Phase behavior samples are made by first preparing surfactant stock solutions and combining them with brine stock solutions in order to observe the behavior of the mixtures over a range of salinities. All the experiments are created at or above 0.1 wt % active surfactant concentration, which is above the typical CMC of the surfactant.

Solution Preparation. Surfactant stocks are based on active weight-percent surfactant (and co-surfactant when incorporated). The masses of surfactant, co-surfactant, co-solvent and de-ionized water (DI) are measured out on a balance and mixed in glass jars using magnetic stir bars. The order of addition is recorded on a mixing sheet along with actual masses added and the pH of the final solution. Brine solutions are created at the necessary weight percent concentrations for making the scans.

Surfactant Stock. The chemicals being tested are first mixed in a concentrated stock solution that usually consisted of a primary surfactant, co-solvent and/or co-surfactant along with de-ionized water. The quantity of chemical added is calculated based on activity and measured by weight percent of total solution. Initial experiments are at about 1-3% active surfactant so that the volume of the middle microemulsion phase would be large enough for accurate measurements assuming a solubilization ratio of at least 10 at optimum salinity.

Polymer Stock. Often these stocks were quite viscous and made pipetting difficult so they are diluted with de-ionized water accordingly to improve ease of handling. Mixtures with polymer are made only for those surfactant formulations that showed good behavior and merited additional study for possible testing in core floods. Consequently, scans including polymer are limited since they are done only as a final evaluation of compatibility with the surfactant.

Pipetting Procedure. Phase behavior components are added volumetrically into 5 ml pipettes using an Eppendorf Repeater Plus or similar pipetting instrument. Surfactant and brine stocks are mixed with DI water into labeled pipettes and brought to temperature before agitation. Almost all of the phase behavior experiments are initially created with a water oil ratio (WOR) of 1:1, which involved mixing 2 ml of the aqueous phase with 2 ml of the evaluated crude oil or hydrocarbon, and different WOR experiments are mixed accordingly. The typical phase behavior scan consisted of 10-20 pipettes, each pipette being recognized as a data point in the series.

Order of Addition. Consideration had to be given to the addition of the components since the concentrations are often several fold greater than the final concentration. Therefore, an order is established to prevent any adverse effects resulting from surfactant or polymer coming into direct contact with the concentrated electrolytes. The desired sample compositions are made by combining the stocks in the following order: (1) Electrolyte stock(s); (2) Deionized water; (3) Surfactant stock; (4) Polymer stock; and (5) Crude oil or hydrocarbon. Any air bubbles trapped in the bottom of the pipettes are tapped out (prior to the addition of surfactant to avoid bubbles from forming).

Initial Observations. Once the components are added to the pipettes, sufficient time is allotted to allow all the fluid to drain down the sides. Then aqueous fluid levels are recorded before the addition of oil. These measurements are marked on record sheets. Levels and interfaces are recorded on these documents with comments over several days and additional sheets are printed as necessary.

Sealing and Mixing. The pipettes are blanketed with argon gas to prevent the ignition of any volatile gas present by the flame sealing procedure. The tubes are then sealed with the propane-oxygen torch to prevent loss of additional volatiles when placed in the oven. Pipettes are arranged on the racks to coincide with the change in the scan variable. Once the phase behavior scan is given sufficient time to reach reservoir temperature (15-30 minutes), the pipettes are inverted several times provide adequate mixing. Tubes are observed for low tension upon mixing by looking at droplet size and how uniform the mixture appeared. Then the solutions are allowed to equilibrate over time and interface levels are recorded to determine equilibration time and surfactant performance.

Measurements and Observations. Phase behavior samples are allowed to equilibrate in oven that is set to the reservoir temperature for the crude oil being tested. The fluid levels in the pipettes are recorded periodically and the trend in the phase behavior observed over time. Equilibrium behavior is assumed when fluid levels ceased to change within the margin of error for reading the samples.

Fluid Interfaces. The fluid interfaces are the most crucial element of phase behavior experiments. From them, the phase volumes are determined and the solubilization ratios are calculated. The top and bottom interfaces are recorded as the scan transitioned from an oil-in-water micro emulsion to a water-in-oil microemulsion. Initial readings are taken one day after initial agitation and sometimes within hours of agitation if coalescence appeared to happen rapidly. Measurements are taken thereafter at increasing time intervals (for example, one day, four days, one week, two Weeks, one month and so on) until equilibrium is reached or the experiment is deemed unessential or uninteresting for continued observation.

If the interfaces are hard to read, a 365 nm black light is used to illuminate the micro emulsion phase and to improve the contrast between the micro emulsion and the excess oleic phase.

FIG. 2 shows the structure of alkane sulfonate-sulfate according to one embodiment of the present invention. FIG. 3 shows the structure of the dialkylphenol alkoxylate sulfonate sulfate according to one embodiment of the present invention. FIG. 4 is a schematic representation of the synthesis method for the alkane sulfonate sulfate surfactant. FIG. 5 is a schematic representation of the synthesis method for the Dialkylphenol alkoxylate sulfonate sulfate surfactant.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 5,074,358: Surfactant-stabilized foams for enhanced oil recovery.
United States Patent Application No. 20080196893: Process for oil recovery using mixed surfactant composition.
Dwarkanath, et al., "Using Co-solvents to provide gradients and improve oil recovery during chemical flooding in a light oil reservoir" Paper SPE 113965 presented at the 2008 SPE improved oil recovery symposium, Tulsa, Okla. 19-23 Apr. 2008.

What is claimed is:

1. A method of treating a hydrocarbon-bearing formation, the method comprising:
(a) selecting a composition comprising a cleavable di-functional anionic surfactant, wherein the di-functional anionic surfactant is sufficiently soluble in water such that the di-functional anionic surfactant can be injected into the hydrocarbon-bearing formation; and
(b) injecting the composition into the hydrocarbon-bearing formation, wherein the di-functional anionic surfactant cleaves and releases a highly surface active mono-functional sulfonate in the formation.

2. The method of claim 1, wherein the composition further comprises a sacrificial surfactant.

3. The method of claim 2, wherein the di-functional anionic surfactant is selected from the group consisting di-functional anionic surfactants of the formula (I), the di-functional anionic surfactants of formula (II), and a combination thereof:

4. The method of claim 3, wherein the sacrificial surfactant is selected from the group consisting of dialkyl sulfosuccinates and their alkoxylated homologues, monoalkyl sulfosuccinates and their alkoxylated versions, mono alkyl succinates and their alkoxylated versions, and alcohol alkoxysulfates.

5. The method of claim 4, wherein the dialkyl sulfosuccinates, monoalkyl sulfosuccinates, and mono alkyl succinates comprise linear or branched $C_4$-$C_{16}$ saturated or unsaturated chains, polyethoxy or polypropoxy chains with a degree of polymerization ranging from 0-12, $C_4$-$C_{12}$ alkylphenol structures or combinations thereof.

6. The method of claim 4, wherein the alcohol alkoxysulfates comprise linear or branched $C_6$-$C_{32}$ chains, polyethoxy or polypropoxy chains with a degree of polymerization ranging from 0-50, $C_4$-$C_{12}$ alkylphenol structures or combinations thereof.

7. The method of claim 1, wherein the sacrificial surfactant is hydrolyzable and forms an alcohol under downhole conditions.

8. The method of claim 1, wherein the hydrocarbon-bearing formation is downhole.

9. The method of claim 8, wherein the downhole conditions comprise a pressure in a range from about 1 bar to 1000 bars and a temperature in a range of from about 70° F. to 400° F.

10. The method of claim 1, further comprising fracturing the hydrocarbon formation, wherein the composition is injected into the hydrocarbon bearing formation during the fracturing, after the fracturing, or both during and after fracturing.

11. The method of claim 1, wherein the hydrocarbon-bearing formation has a wellbore therein, the method further comprising obtaining hydrocarbons from the wellbore after injecting the composition into the it hydrocarbon-bearing formation.

12. The method of claim 1, wherein the di-functional anionic surfactant is of the formula (I):

wherein
(a) $R_1$ and $R_2$ are the same or different,
(b) $R_1$ and $R_2$ are each an alkyl group or hydrogen; and
(c) $R_1$ and $R_2$ combined comprise 10 to 40 carbon atoms.

13. The method of claim 12, wherein $R_1$ and $R_2$ are each an alkyl group.

14. The method of claim 1, wherein the di-functional anionic surfactant is of the formula (II):

wherein
(a) $R_1$ and $R_2$ are the same or different,
(b) $R_1$ and $R_2$ are each an alkyl group or hydrogen; and
(c) $R_1$ and $R_2$ combined comprise 10 to 40 carbon atoms.

15. The method of claim 14, wherein $R_1$ and $R_2$ are each an alkyl group.

16. The method of claim 1, wherein the composition is cleavable at reservoir pH, temperature, pressure, or a combination thereof.

17. The method of claim 1, wherein the composition comprises a high molecular weight sulfated internal olefin sulfonate.

18. The method of claim 1, wherein the composition comprises a high molecular weight Dialkylphenol alkoxylate sulfonate sulfate.

19. A method of treating a hydrocarbon-bearing formation comprising:
(a) selecting a composition comprising a cleavable di-functional anionic surfactant and a sacrificial surfactant, wherein the combination of the di-functional anionic surfactant and the sacrificial surfactant is sufficiently soluble in water such that combination can be injected into the hydrocarbon-hearing formation; and
(b) injecting the composition into the hydrocarbon-bearing formation, wherein the di-functional anionic surfactant cleaves and releases a highly surface active mono-functional sulfonate in the formation.

20. The method of claim 19, wherein the sacrificial surfactant is hydrolyzable and form an alcohol under downhole conditions.

* * * * *